United States Patent [19]

Magram

[11] Patent Number: 5,405,316
[45] Date of Patent: Apr. 11, 1995

[54] CEREBROSPINAL FLUID SHUNT

[76] Inventor: Gary Magram, 402 Faulk Rd., Apt. 6B12, Wilmington, Del. 19803

[21] Appl. No.: 153,517

[22] Filed: Nov. 17, 1993

[51] Int. Cl.$^6$ .................................................. A61M 5/00
[52] U.S. Cl. ........................................ 604/8; 604/175; 604/264
[58] Field of Search ..................................... 604/7–10, 604/175, 247, 280, 282, 264

[56] References Cited

U.S. PATENT DOCUMENTS

| | | |
|---|---|---|
| 2,969,066 | 1/1961 | Holter et al. . |
| 3,111,125 | 11/1963 | Schulte ................................. 604/9 |
| 3,288,142 | 11/1966 | Hakim . |
| 3,583,387 | 6/1971 | Garner et al. . |
| 3,595,240 | 7/1971 | Mishler . |
| 3,601,128 | 8/1971 | Hakim . |
| 3,889,687 | 6/1975 | Harris et al. . |
| 3,938,529 | 2/1976 | Gibbons ........................... 604/282 |
| 4,103,689 | 8/1978 | Leighton . |
| 4,605,395 | 8/1986 | Rose et al. . |
| 4,621,654 | 11/1986 | Holter . |
| 4,737,153 | 4/1988 | Shimamura et al. ................. 604/282 |
| 4,767,400 | 8/1988 | Miller et al. . |
| 4,850,955 | 7/1989 | Newkirk ................................. 604/8 |
| 5,000,731 | 3/1991 | Wong et al. . |
| 5,069,674 | 12/1991 | Fearnot et al. ...................... 604/282 |

OTHER PUBLICATIONS

B. Magnaes, "Movement of Cerebrospinal Fluid within the Craniospinal Space when Sitting Up and Lying Down," *Surg. Neurol.*, vol. 10, Jul. 1978, pp. 45–49.

S. Hashimoto et al., "A Newly Designed Flow-Regulating Device in Shunt Therapy of Hydrocephalus," *Artif Organs*, vol. 13, No. 5, 1989, pp. 483–485.

D. J. Gower et al., "e-PTFE Ventricular Shunt Catheters," *Neurosurgery*, vol. 31, No. 6, Dec. 1992, pp. 1132–1135.

*Primary Examiner*—Jerome L. Kruter
*Attorney, Agent, or Firm*—Lowe, Price, LeBlanc & Becker

[57] ABSTRACT

A cerebrospinal fluid shunt includes an inner tube for supplying the fluid only from brain ventricles to the peritoneum region of a subject and an outer tube arranged so the fluid remains resident in the outer tube without flowing to the peritoneum region. Fluid in the outer tube exerts pressure through a wall of the inner tube on the fluid in the inner tube to regulate flow of the fluid through the inner tube to the peritoneum region. The shunt includes a catheter including plural openings through which the fluid flows. The openings are arranged so tissue growth through the openings does not occlude flow of the fluid within the catheter. The catheter and shunt having an external pressure responsive collapsible wall and an internal spring for inhibiting catheter collapsing and kinking.

36 Claims, 4 Drawing Sheets

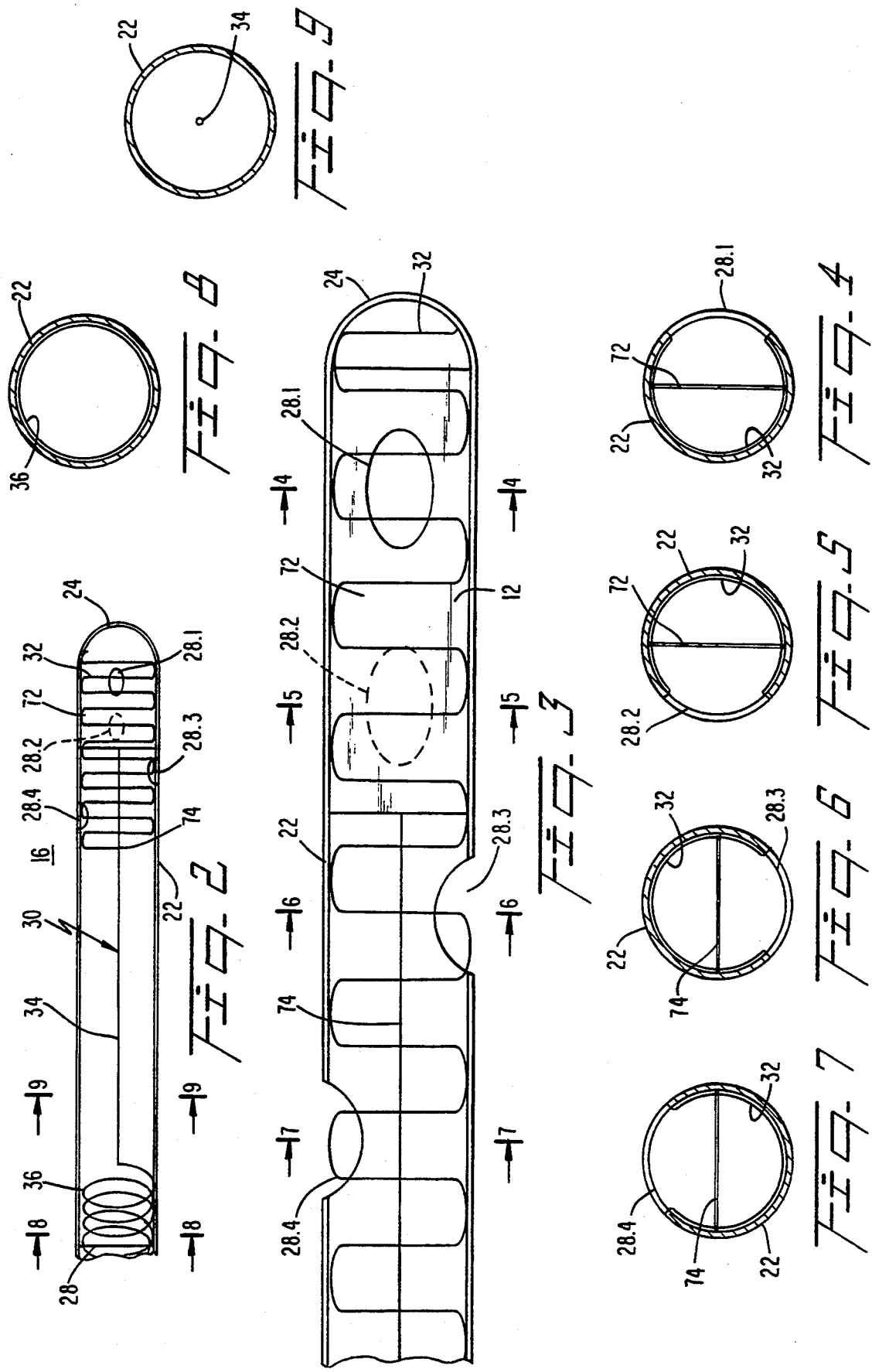

CEREBROSPINAL FLUID SHUNT

FIELD OF INVENTION

The present invention relates generally to a shunt for the flow of cerebrospinal fluid between brain ventricles and a peritoneum region of a subject and more particularly to such a shunt including an inner tube for supplying the fluid only from the brain ventricles to the peritoneum region and an outer tube arranged so the fluid from the brain ventricles is resident in the outer tube without flowing to the peritoneum region and the fluid in the outer tube exerts pressure through a wall of the inner tube on the fluid in the inner tube to regulate flow of the fluid through the inner tube to the peritoneum region. The invention also relates to a catheter, and more particularly to a catheter including plural openings through which internal body fluid flows, wherein the openings are arranged so non-fluid material, e.g., tissue growth, into the openings does not occlude flow of the fluid within the catheter. The invention also relates to a catheter having an external pressure responsive collapsible wall and an internal structure for inhibiting collapsing and kinking of the catheter.

BACKGROUND ART

The intracranial pressure of a mammal subject results from a complex sum of pressures and volume changes within the central nervous system of the subject. The skull generally protects the central nervous system from external deforming forces. In a child with an open fontanelle ("soft spot" on the head of an infant), the cranial vault is likely to be deformed leading to increased intracranial pressure or displacement of brain tissue. When a tight head dressing is applied, venous blood frequently does not freely flow into the scalp with a resultant increase in intracranial pressure. Intracranial volume changes can result from increases in the cerebrovascular blood volume, intracranial bleeding, infections, cerebritis, abscesses or empyemas, increases in brain tissue such as central nervous system tumors and disequilibrium between the cerebrospinal fluid production and absorption. Changes in intra-abdominal pressure, as caused by e.g. coughing and sneezing, can be transmitted by the epidural venous plexus to the intracranial cerebrospinal fluid (CSF) compartment. Respiratory variations due to inhaling and exhaling can affect venous return to the heart and cardiac pulsations can result in pressure and volume changes in the cerebrovascular system.

Because the CSF is compartmentalized, an increase in pressure in one compartment can result in CSF flowing into an adjacent compartment, i.e. a circulation of CSF. Choroid plexus pulsations can promote flow out of the ventricular system and venous epidural pulsations move CSF out of the intraspinal compartment. Brain expansion from increases in cerebrovascular blood volume helps CSF flow out of cisterns containing fluid sacs. When treating diseases affecting intracranial pressure it is important to try to re-establish CSF circulation and to normalize the intracranial pressure. In an attempt to resolve these problems, brain ventricle to peritoneum shunts have been developed to supply CSF from the brain to the peritoneum of the subject.

A problem with prior art ventricle to peritoneum shunts is that they do not restore the CSF circulation lumbar shunt must initially have excessive tubing; otherwise the shunt must be removed and replaced from time to time. A solution is to insert a large loop of excessive tubing into the peritoneal cavity. The tubing is pulled outward as the subject grows both in height and circumferentially.

Subjects with syringomyelia and craniocerival junction abnormalities, including the Chiari malformations, may be amenable to a bypass. Syringomyelia is associated with a change in the CSF accumulator function. When fluid pulse waves cannot be easily transferred up and down the spine, the spinal cord is subjected to "shock waves." Ordinarily, fluid pressure changes cause the CSF to flow parallel to the spinal cord so the resulting force vector is parallel to the spinal cord axis. When there is an obstruction to CSF flow and CSF cannot be displaced into another compartment, the fluid pulse waves cause a temporary pressure elevation in the obstructed compartments. If the force vector of the fluid pulse waves is not parallel to the spinal cord but angled towards the perpendicular, the force is transmitted into the spinal cord. The spinal cord portion having the lowest resistance to the force vector is thereby subjected to the shock waves and can become a pathological site for CSF accumulation. The resistance is lowest at the softest spinal cord sites or those having the highest water content. Hence, gray matter has a lower resistance than white matter and softened spinal cord from ischemic changes or traumatic changes is more subject to syrinx formation.

CSF flows into the spinal cord when the shock wave pressure exceeds the resistance of a portion of the spinal cord. If the pressure outside the spinal cord is significantly greater than the pressure inside the cord and the resulting pressure differential is greater than the force vector resistance, CSF can flow in towards the although they provide a decrease in intracranial pressure. When a subject has a raised intracranial pressure associated with a block in CSF circulation, the present treatment of choice is to surgically relieve the obstruction, either by removing the obstructing lesion or creating a communication between an obstructed compartment and the open CSF circulation. An example of the former is removal of a posterior fossa tumor to alleviate a fourth ventricular obstruction. An example of the latter is forming a third ventriculostomy in a subject with a benign tectal glimoa leading to aqueductal obstruction.

When neither of these alternatives is feasible an attempt may be made to bypass the obstruction by inserting a shunt from the obstructed compartment to the open CSF circulation. An example is a patient with a nonresectable hypothalamic optic pathway glioma causing an obstruction at the level of the third ventricle. In this situation the two lateral ventricles are coupled together by surgically opening the septumpellucidum. A ventricular catheter with proximal and distal holes is connected with distal tubing going into the lumbar thecal sac to drain both lateral ventricles. The resulting overdrainage into the lumbar thecal cavity restores the CSF circulation and there is no siphoning effect to be offset as with a brain ventricle peritoneum shunt. The lumbar sac is chosen because it does not interfere with the spinal cord, which at higher spinal levels could be traumatized by insertion of a shunt. A shunt going from the ventricular to the cisterna magna or subarachnoid space is also a possibility. Insertion of a shunt to the subarachnoid space over the convexity of the brain requires a craniotomy and an alternative material to the standard silicone elastomer. Silicone elastomers can lead to very thin membranes and loculation of the CSF in the subarachnoid space. However, in a growing child a cord. When the pressure outside the spinal cord lessens and is not significantly less than the cavitary pressure, the pressure might not be able to overcome the resistance of the spinal cord so CSF may not flow out of the syrinx into the subarachnoid space. Thus, transient pulsations in the intrathecal sac can lead to a "pumping up" of a syrinx within the spinal cord until the pressure within and outside the cord are equal. This accumulation tends to be greatest at regions where the force vector is most angled inward towards the curve, such as the normal cervical lordosis or in regions adjacent a kyphoscoliotic curvature. The accumulation tends to be greatest in the regions of the spinal cord where there is the most gray matter or the cord is softened due to some other pathological process, such as being compressed against the spinal canal in a kyphoscoliosis. This theory is consistent with having a syrinx formation at the C5-6 level in association with a Chiari malformation and small syrinx formation associated with scoliotic curvatures. This also explains the formation of syrinxes in the lumbar enlargement where there is more gray matter in subjects with tethered cords.

Inserting a syringosubarachnoid shunt lowers the resistance to flow between the syrinx cavity and subarachnoid space, thus allowing the syrinx to be more easily deflated when intraspinal subarachnoid pressures are lowered. In scoliosis, the cord is stretched over the concave portion of the spinal column curve, leading to softening of the curve and a lower resistance for CSF entrance. Since the CSF does not travel in a straight path, a shock wave pounds against the spinal cord just proximal to the curve and a syrinx can develop.

For a subject having a Chiari malformation, the shock wave strikes the spinal cord at the area of the greatest cervical lordosis. Thence, the resistance to the force vector from the shock wave is lowest in the portion of the cord with the greatest proportion of gray matter. Consequently, the syrinx often begins at the C5-6 level. The initial treatment for a syrinx with an obstruction at the craniocervical junction is to remove the odontoid process transorally if there is a ventral impingement. Such removal attempts to alleviate the obstruction and re-establish flow.

A posterior compression with duraplasty for a tight posterior fossa is an alternative treatment. The duraplasty can act as a pseudo meningocele reservoir and function as an accumulator. Despite a posterior fossa decompression and opening of the dura, the subject sometimes later develops an arachnoiditis. This can be near the suture line of the dural patch. This arachnoiditis can restrict the free flow of CSF, causing the subject to redevelop the syrinx.

In an effort to try to keep a pathway open, a stent can be inserted; however, the stent also can become obstructed, especially if there is already a stimulus for scar formation. Placing a stent from the syrinx to the subarachnoid space helps to equalize the pressure but is also prone to obstruction in the long run. Draining the syrinx to lower the pressure helps it to collapse even further so a syrinx to pleural or peritoneal shunt can be successful.

Another alternative is to provide a lower resistance pathway for CSF to return to the open CSF circulation such as with a shunt from the spinal subarachnoid space to the fourth ventricle or lateral cisterns. A problem with this approach is that sometimes the proximal end of the shunt irritates one of the cranial nerves in the lateral cisterns, causing the subject to have headaches, neck pain or other cranial nerve dysfunctions. If the shunt is on the floor of the fourth ventricle, it may irritate this area, with the patient experiencing postoperative nausea and vomiting. Shunting from the intraspinal subarachnoid space to the lateral ventricles might be less irritating and does not require a posterior fossa exposure. Placement of such a shunt is technically straightforward and a catheter can be placed percutaneously into the lumbar dural sac, tunneled up to the head and then placed into the lateral ventricle by way of a bur hole. An expandable reservoir can be interposed to act as an accumulator.

Another approach is to tunnel an intraspinal catheter up to the vertex of the head with distensible tubing interposed. At the vertex, the intraspinal catheter can be attached to an anti-siphon or siphon control device and then tunneled down to a distal cavity such as the pleura or peritoneum. This prevents overdrainage of CSF but allows easy escape of CSF if there is a positive pressure. Scarring around the antisiphon device alters coupling of atmospheric pressure to the CSF, leading to a malfunction of the shunt system. In subjects having external hydrocephalus from either a meningitis or subarachnoid hemorrhage, the obstruction cannot be bypassed to provide CSF reabsorption. In these situations the CSF is either diverted directly into the venous sinus or into another body cavity for absorption. A prior art brain ventricle to peritoneum shunt does not have accumulator capabilities, causing CSF circulation to remain abnormal, although it can control intracranial pressure (ICP). Thus, whenever CSF circulation receives a positive fluid pulse pressure, CSF exits by way of the shunt but when a negative fluid pulse pressure follows, CSF does not return to the CSF circulation. Until the lost CSF is produced, this negative pressure results in an increase in either the brain volume or intracranial blood volume. Thus the pulsatile intracranial pressure results in a gradual progressive emptying of the CSF compartments.

A possible solution to the problem of the CSF compartments gradually emptying through the use of prior art shunts is to attach the ventricular catheter to a three-way connector. From this connector, (a) one valveless tube is connected to the intraspinal subarachnoid space and (b) another tube having a valve goes to the distal body cavity. With this arrangement, the spinal subarachnoid space assumes an accumulator function. The resistance for CSF flow to the intraspinal compartment would be much less than the added resistance offered by the valve. However, there are several problems with this arrangement. First, it is a relatively complicated setup. Second, when the subject stands erect there must be an anti-siphon device proximal the distal cavity to prevent overdrainage or a flow control device must be inserted. Third, the intraspinal subarachnoid space is often involved in the disease process and cannot provide free circulation of CSF and therefore is severely limited in its accumulator function.

It is accordingly an object of the present invention to provide a new and improved shunt for regulating the flow of cerebrospinal fluid from the brain ventricles to the peritoneum of a subject to overcome the aforementioned problems.

Another object of the invention is to provide such a shunt for regulating CSF flow relatively independently of whether the subject is upright or lying down.

An additional object is to provide such a shunt wherein CSF flow is regulated somewhat independently of pressure pulses within the subject, due e.g. to coughing or sneezing.

A further object is to provide such a shunt that is relatively easy to remove from a subject to accommodate changes in the size of the subject, due, e.g. to growth of a child.

An added object is to provide such a shunt with a brain ventricle catheter having plural openings in a proximal end thereof, which openings are arranged to prevent occlusion of CSF within the catheter.

A further object is to provide such a shunt with a brain ventricle catheter having a structure and plural openings arranged so tissue cannot grow from openings on opposite side wall portions of the catheter.

An additional object of the invention is to provide such a shunt with a pressure responsive deformable outer wall for coupling pressure variations from within a subject to CSF flowing from the brain to the peritoneum.

Yet a further object is to provide a catheter with a pressure responsive deformable outer wall for coupling pressure variations from within a subject to fluid within the catheter, wherein the catheter includes internal structure for inhibiting collapsing and/or kinking thereof.

Yet another object of the invention is to provide a new and improved catheter having a structure and plural openings in a proximal end thereof, which openings are arranged to prevent occlusion of fluid within the catheter.

DISCLOSURE OF THE INVENTION

In accordance with one aspect of the invention, a shunt for the flow of cerebrospinal fluid between brain ventricles and a peritoneum region of a subject comprises a first tube for supplying the fluid only from the brain ventricles to the peritoneum region. A second tube around the first tube is arranged so the fluid from the brain ventricles remains resident in the second tube without flowing to the peritoneum region. The first tube is constructed so the fluid in the second tube exerts pressure through a wall of the first tube on the fluid in the first tube. The first and second tubes are constructed so that in response to the volume of fluid in the second tube increasing there is an increase in pressure through the first tube wall on the fluid in the first tube and vice versa for decreases in the fluid volume in the second tube.

Preferably, the wall of the first tube is collapsible so the wall moves toward the center of the first tube in response to the pressure on the exterior of the wall of the first tube exceeding the pressure on the interior of the wall of the first tube and vice versa.

The wall of the second tube is also preferably collapsible so the wall of the second tube moves toward the wall of the first tube in response to the pressure on the exterior of the wall of the second tube exceeding the pressure on the interior of the wall of the second tube and vice versa. The compliance of the first tube is preferably greater than that of the second tube so pressure changes in the fluid in the second tube have a greater effect on the fluid in the first tube than external pressure changes have on fluid in the second tube. This is important for proper regulation of flow of the fluid as the subject changes position, e.g., from standing to lying down, and for changes in pressure within the subject relative to the intracranial pressure of the fluid due, e.g., to coughing and sneezing.

To assist in attaining these results the first and second tubes are constructed and arranged so the first tube has a cross-sectional area (a) in a first range in response to pressure from the fluid on an interior wall of the second tube having a neutral value associated with the pressure on the interior wall approximating atmospheric pressure, (b) in a second range in response to pressure from the fluid on the interior wall of the second tube having a value in excess of atmospheric pressure, and (c) in a third range in response to the pressure from the fluid on the interior wall of the second tube having a value less than atmospheric pressure. The values in the second and third ranges are respectively greater and less than the values in the first range.

The first and second tubes are preferably constructed and arranged so the first tube has (a) a first oval-like cross-sectional area in response to pressure from the fluid on the interior wall of the second tube having the neutral value, (b) a second oval-like cross-sectional area with a longer major axis than the first oval-like cross in response to pressure from the fluid on the interior wall of the second tube having a value in excess of atmospheric pressure, and (c) a circular-like cross-section in response to the pressure of the fluid on the interior wall of the second tube having a value less than atmospheric pressure.

Alternatively, the first and second tubes are constructed and arranged so the first tube has (a) a first oval-like cross-sectional area in a first range in response to pressure of the fluid on an interior wall of the second tube having a neutral value associated with the pressure on the interior wall approximating atmospheric pressure, (b) an oval-like cross-sectional area with a major axis in a first direction in response to pressure of the fluid on the interior wall of the second tube having a value in excess of atmospheric pressure, and (c) an oval-like cross-sectional area with a major axis in a second direction, generally at right angles to the first direction, in response to the pressure of the fluid on the interior wall of the second tube having a value less than atmospheric pressure. The values in the second and third ranges are respectively greater and less than the values in the first range.

In one embodiment, the second tube includes a structure so (a) a first wall portion of the second tube adjacent skin of the subject has a greater radius of curvature than a second wall portion of the second tube adjacent inner fascia of the subject in response to the pressure of the fluid on the interior wall of the second tube having a value less than atmospheric pressure. These radii of curvature have centers on the same side of the second wall portion when the pressure of the fluid on the interior wall of the second tube has a value less than atmospheric. The first and second wall portions have oppositely directed curvatures relative to the center of the first tube in response to the pressure of the fluid on the interior wall of the second tube having a value greater than atmospheric pressure. The aforementioned structure includes a spring preferably bearing against the interior wall of the second tube and made of a plastic material that does not cut through the second tube. The spring has plural axially spaced hemispherical sections bearing against a first wall portion to the exclusion of a diametrically opposed second wall portion.

To assist in providing the aforementioned cross-sectional area sizes and shapes, in one embodiment the first wall portion of the second tube is stiffer and has a greater extent around the perimeter of the second tube than the second wall portion of the second tube when the pressure of the fluid on the interior wall of the second tube has a value approximately equal to atmospheric pressure.

A portion of the first tube facing the first wall portion of the second tube is mechanically connected to an interior segment of the first wall portion about half way between opposite ends of the first wall portion and a region of the first tube facing the second wall portion of the second tube is mechanically connected to an interior segment of the second wall portion about half way between opposite ends of the second wall portion.

In accordance with another aspect a catheter, preferably for ventricular fluid flow from the brain, includes a tube with a wall having plural openings positioned and arranged to prevent non-fluid material of the subject from occluding the flow of fluid through the catheter. Preferably, all of the plural openings are axially spaced from each other along the length of the catheter and are positioned at different angles about the catheter wall.

A member within the catheter in a region extending across first and second of said openings divides the region into first and second chambers. Thereby, material from the subject entering the first chamber through the first opening is inhibited from entering the second chamber and does not traverse the second opening and material from the subject entering the second chamber through the second opening is inhibited from entering the first chamber and does not traverse the first opening.

In a preferred embodiment, the catheter wall includes first, second, third and fourth of openings. The first and second openings are on portions of the catheter wall that are spaced from each other by about 180°, while the third and fourth openings are on portions of the catheter wall that are spaced from each other by about 180° and from the first and second openings by about 90°. First and second members are at first and second axially displaced regions within the catheter. The first member divides the first region into first and second chambers and is approximately at right angles to the second member which divides the second region into third and fourth chambers. The first, second, third and fourth openings respectively open into the first, second, third and fourth chambers. The members, openings and chambers are arranged so non-fluid material from the subject entering one of the chambers through the opening of that chamber is inhibited from entering the other chambers and does not traverse the other openings.

In accordance with another aspect of the invention, a catheter, preferably for draining fluid from the brain ventricles, includes a collapsible wall and mechanical means within the catheter for inhibiting collapsing and-/or kinking of the catheter wall. The mechanical means preferably includes a spring bearing against interior portions of the catheter wall. The spring preferably includes first and second connected segments respectively bearing against proximal and distal ends of the interior of the catheter wall.

BRIEF DESCRIPTION OF THE DRAWING

FIG. 2 is a perspective view of a ventricular catheter included in the apparatus illustrated in FIG. 1;

FIG. 3 is a longitudinal cross sectional view of a proximal region of the catheter illustrated in FIG. 2;

FIGS. 4–7 are cross sectional views of the structure illustrated in FIG. 3, respectively taken through the lines 4—4, 5—5, 6—6, and 7—7;

FIG. 8 is a cross sectional view from the distal end of the ventricular catheter illustrated in FIG. 2, taken through the lines 8—8;

FIG. 9 is a cross sectional view of a medial portion of the catheter illustrated in FIG. 2, taken through the lines 9—9;

DESCRIPTION OF THE PREFERRED EMBODIMENTS

Figure 1:
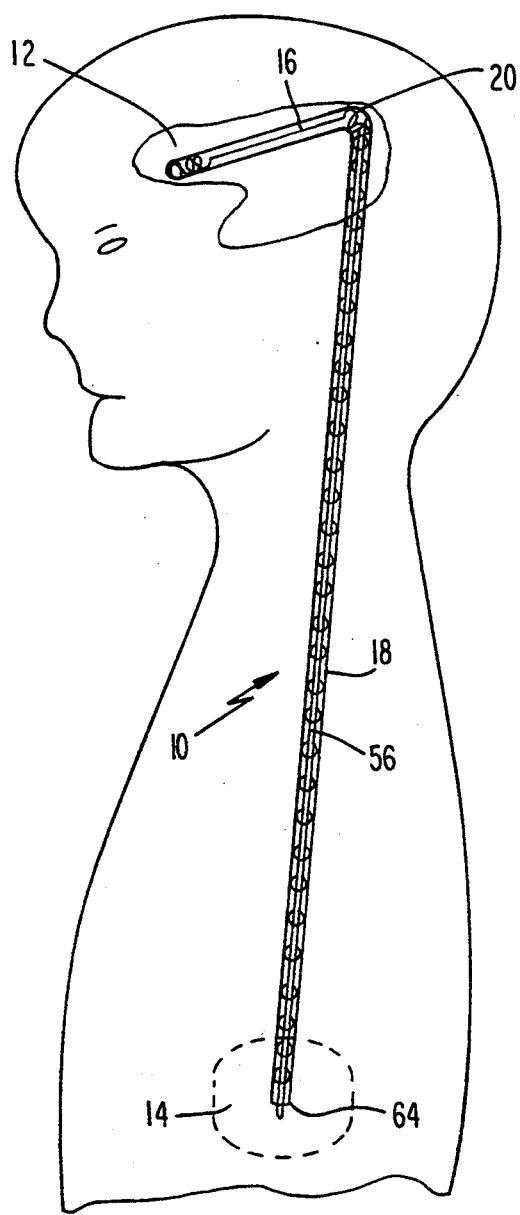
FIG. 1 is a schematic perspective drawing of a preferred embodiment of a CSF shunt in accordance with the invention.

Reference is now made to FIG. 1 of the drawing, wherein a preferred embodiment of shunt 10 for the flow of cerebrospinal fluid (CSF) between brain ventricles 12 and a peritoneum region 14 of a subject is illustrated as including ventricle brain catheter 16 and distal subcutaneous shunt 18, connected together by bent tube region 20. Catheter 16, shunt 18 and region 20 are integrally formed, with ends thereof being bonded together.

Shunt 18 includes two concentric, coaxial tubes made of pressure responsive deformable, i.e. compressible, material, with the inner tube being softer and more compliant than the outer tube. The outer tube of shunt 18 is open at the proximal end of shunt 18 so the cerebrospinal fluid from brain ventricles 12 flows into the outer tube. However, the distal end of the outer tube of shunt 18 is closed so the cerebrospinal fluid has a tendency to accumulate or fill in the outer tube. The inner tube of shunt 18 has a check valve at its distal end, permitting the flow of cerebrospinal fluid from the brain ventricles to the peritoneum region, while preventing fluid from flowing from the peritoneum region to the interior of the inner tube and thence to the brain.

With increasing and decreasing volumes of fluid in the outer tube of shunt 18, which functions basically as a reservoir or accumulator, there are concomitant increases and decreases of pressure exerted through the walls of the inner tube on fluid within the inner tube to control the flow of cerebrospinal fluid from the brain ventricles to the peritoneum region, once fluid starts to flow between these two sites.

Hence, CSF is appropriately drained from ventricles 12 so that if there is an excess amount of CSF in the ventricles there is a relatively large amount of CSF flowing to peritoneum region 14 and if there is no excess CSF in ventricles 12 there is little or no CSF flow to peritoneum 14. When the subject is standing, the hydrostatic pressure to the fluid column in the outside tube of shunt 18 increases the external pressure on the inner, collapsible tube, to offset the hydrostatic pressure of the CSF column in the inner tube. As the CSF leaves the inner tube, the inner tube tends to collapse because of the external hydrostatic pressure. This construction makes CSF flow in shunt 18 independently of gravitational effects, due, e.g. to a subject standing or lying down. CSF flow in shunt 18 is thus dependent primarily on the differential pressure between the fluids in brain ventricles 12 and peritoneum region 14. Because of the compliance of the outer tube, pressure increases and decreases on the outer tube of shunt 18 relative to the pressure of the CSF within the inner tube of shunt 18 (due e.g. to inhaling, exhaling, coughing, sneezing or atmospheric pressure changes) do not materially affect the CSF flow rate to peritoneum region 14. Such pressure changes are coupled through the somewhat compliant wall of the outer tube and coupled via a structure between walls of the outer and inner tubes to the inner tube to change the inner tube cross-sectional area and volume. For pressures on the outer wall of the outer tube greater and smaller than the CSF inside the tubes, there are concomitant decreases and increases in the cross-sectional area and volume of the inner tube.

Consideration is now given to the various details of preferred embodiments of shunt 10, by referring, initially, to the perspective view of ventricular catheter 16, as illustrated in FIG. 2. Ventricular catheter 16 includes a collapsible pressure responsive tube 22 preferably made of a plastic or silastic elastomer, such as expanded polytetrafluorotethylene (e-PTFE), and having an outer diameter of about 10 mm and a wall thickness of about 0.5 mm. Proximal and distal ends 24 and 26 of tube 22 are respectively closed and open; however, a series of openings 28 subsists along the length of tube 22 just behind proximal end 24. In the vicinity of openings 28, in the distal region of tube 22 there are two internal diametrically extending membranes within tube 22 to assist in preventing occlusion of catheter 14. The two membranes separate the distal region of catheter 16 into two compartments which are in fluid flow communication with each other, so the entire interior of tube 22 can be considered as a single chamber, for fluid flow purposes.

Occlusion of catheter 14 would prevent the flow of CSF into and through the catheter to region 20 and distal subcutaneous shunt 18. If a catheter has a single opening such occlusion is likely because there is a tendency for cells from the subject to grow in such a hole and block CSF flow. If two diametrically opposed holes are provided there is a likelihood of the growth extending into one of the holes and out of the other hole. Such a construction is likely to lead to occlusion and makes catheter removal difficult.

To prevent tube 22 from collapsing, spring 30 is inserted therein. Spring 30 includes a relatively long hemispherical section 32 proximate openings 28, a straight, axially extending section 34 and a relatively short helical section 36 at distal end 26 of tube 22. Flexible spring 30 is made of an inert plastic material, for example TEFLON, that cannot penetrate through the walls of tube 22. Spring sections 32 and 36 bear against the interior wall of tube 22 to prevent collapse and/or kinking and/or shortening of tube 22 while maintaining the flexibility of the tube and the ability of fluid pressure to be transmitted through the wall of tube 22.

Reference is now made to FIGS. 3–7 wherein the proximal region of catheter 16 is illustrated in detail as including elongated openings 28.1, 28.2, 28.3 and 28.4, spaced longitudinally and circumferentially from each other. Each of openings 28.1–28.4 preferably has an axial extent of about 2 mm and a circumferential extent of about 1 mm. Openings 28.1 and 28.2, in the forward portion of the proximal region of catheter 16, are located on opposite sides of circular cross section wall 22, being arcuately displaced approximately 180° from each other. Openings 28.3 and 28.4, located rearwardly of opening 28.2, are also arcuately displaced 180° from each other, but are arcuately displaced 90° from openings 28.1 and 28.2. In one embodiment, adjacent ends of openings 28.1 and 28.2 are axially spaced 3 mm from each other as are openings 28.3 and 28.4, while adjacent ends of openings 28.2 and 28.3 are axially spaced 4 mm from each other. By axially and arcuately spacing openings 28.1–28.4 relative to each other, excess CSF from brain ventricles 12 inevitably flows into the interior of catheter 16.

Compliant sheet-like, preferably GORE-TEX membranes 72 and 74, located within the proximal region of catheter 16, extend diametrically across and axially of the catheter. Membrane 72, positioned in the forward portion of the proximal region of catheter 16, extends diametrically across tube 22 in a direction generally parallel to the wall portion of the catheter where openings 28.1 and 28.2 are located. Membrane 74 extends diametrically across tube 22, along the axis of the tube, at right angles to membrane 72. Membrane 72 is in the portion of the catheter where openings 28.1 and 28.2 are located, while membrane 74 extends along the length of tube 20 where openings 28.3 and 28.4 are located. Membranes 72 and 74 are bonded to the interior wall of tube 22 by heat and/or suitable adhesive after spring section 32 has been inserted in place.

Spring section 32 is held in place by having its opposite ends bonded to the interior wall of tube 22. Spring section 32 includes hemispherical segments that extend circumferentially around and abut against the interior wall of tube 22. Adjacent hemispherical segments are connected together so there are "open" portions opposite from the hemispherical segments. As illustrated in FIGS. 4–7 the "open" portions of spring section 32 are coincident with openings 28.1–28.4 and the hemispherical segments of spring section 32 are opposite from these openings. This construction helps to prevent tissue which might grow through openings 28.1–28.4 from being entangled with the spring.

The combination of membranes 72 and 74 and openings 28.1–28.4 is such that complete occlusion of the catheter by ingrowth of tissue into one or more of the openings is substantially prevented. If tissue migrates into one of openings 28.1–28.4, the likelihood of such tissue expanding into the remainder of catheter 16 is quite remote because of the presence and right angle relationship between membranes 72 and 74 and the position thereof relative to openings 28.1–28.4. The axial offset of openings 28.1–28.4 and the presence of membranes 72 and 74 prevents tissue from growing across the interior of tube 22 from one of the openings into and through another of the openings. This construction also enables facile removal of tube 22 because the tube is very unlikely to become mechanically bonded to tissue growing through it.

At the distal end of tube 22, as illustrated in FIG. 8, spring section 36 is bonded to the interior wall of the tube. In the median portion of tube 22, as illustrated in FIG. 9, axially extending strut section 34 of spring 30 extends along the axis of tube 22.

Figure 10:
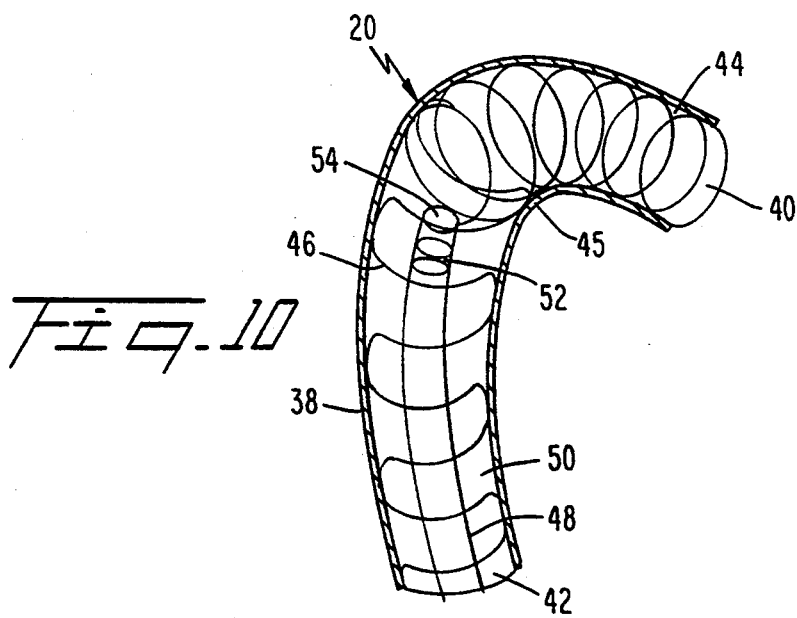
FIG. 10 is a perspective view of a bent region of the CSF shunt illustrated in FIG. 1, which region is connected between the catheter of FIG. 2 and a subcutaneous shunt extending from the head to the peritoneum region of a subject.

Reference is now made to FIG. 10 of the drawing, a perspective view of junction 20 between catheter 16 and shunt 18. Junction 20 includes external collapsible tube 38, having a circular cross section. Tube 38 has open proximal end 40 and open distal end 42 respectively sealingly bonded to tube 22 of catheter 16 and to the external tube of shunt 18. Tube 38 is fabricated of the same material and has the same wall thickness, as well as diameter, as tube 22. Tube 40 includes approximately 120° bend 45 so the portion of the tube adjacent and leading toward proximal end 40 is bent downwardly with respect to the upwardly extending portion of the tube adjacent and leading to distal end 42. Bearing against the interior wall portion of tube 38 between bend 45 and proximal end 40 is inert plastic (preferably TEFLON) helical spring 44, that is easily bent, highly flexible and prevents collapse of tube 38. Bearing against the interior wall portion of tube 44 and between distal end 42 and bend 45 is inert, plastic hemispherical spring 46 (also preferably TEFLON), which permits the portion of tube 38 adjacent and leading to distal end 42 to be flexible, while preventing collapse of the tube.

Extending between the vicinity of bend 45 and distal end 42 of outer tube 38 is internal ultra-thin collapsible tube 48 having a circular cross section; tube 48 preferably is made of e-PTFE or silastic, and has a diameter of approximately 2 mm and a wall thickness of approximately 0.05 mm. The volume between the external wall of internal tube 48 and the internal wall of external tube 38 forms portion 50 of a reservoir for cerebrospinal fluid. To hold internal tube 48 in situ, the external wall of the end of the internal tube adjacent bend 45 has TEFLON ring 52 inserted therein. TEFLON ring 52 is secured to a portion of spring 44 close to bend 45. Thereby, an unobstructed flow path for CSF from catheter 16 is assured to open end 54 of tube 48 and the vertical position of the open end is fixed relative to the remainder of tube 38.

Figure 11:
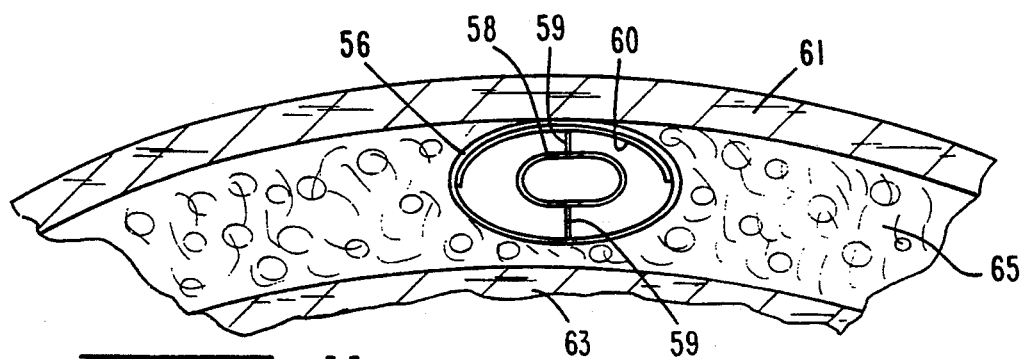
FIG. 11 is a cross sectional view of the subcutaneous shunt extending from the head to the peritoneum region in the subject when the intracranial pressure in a reservoir between a pair of concentric tubes is approximately atmospheric.

As illustrated in FIGS. 1 and 11, shunt 18 includes elongated vertically extending collapsible external tube 56, fabricated of the same material and having the same wall thickness as collapsible tubes 38 and 22. Tube 56 extends through the subcutaneous tissue 65 of the subject. Within collapsible tube 56 is collapsible tube 58, fabricated of the same material and having the same wall thickness as tube 48. Inert plastic, preferably TEFLON, hemispherical spring 60 abuts the inner wall of tube 56 and extends between opposite ends of tube 56. Tubes 56 and 58 have elliptical cross sections when the fluid pressure inside external tube 56 is approximately equal to atmospheric pressure. The external wall of internal tube 58 is connected to the internal wall of tube 56 by flexible struts or membranes 59 that extend in the direction of the common minor axes of the elliptical cross sections forming the tubes. Spring 60 is arranged so the portion thereof abutting the internal wall of external tube 56 always is closer to skin 61 of the subject than the "open" side of the spring which is closer to the portion of tube 58 that is adjacent inner fascia 63 of the subject. Spring 60 is arranged so opposite ends of each hemispherical cross section thereof are farther from the skin of the subject than the major axis of the ellipse forming tube 56 relative to the skin of the subject.

The proximal ends of tubes 56 and 58 are respectively bonded in a sealing relation to the distal ends of tubes 38 and 48 to provide continuous conduits, without holes, from the interior of tube 38 to the interior of tube 56 and from the interior of tube 48 to the interior of tube 58. A connection can be provided between hemispherical spring 60 at the proximal end of shunt 18 and hemispherical spring 46 at the distal end of tube 38.

Figure 12:
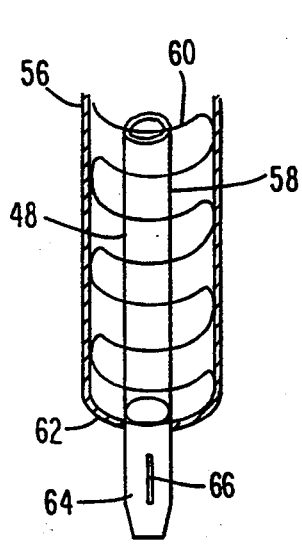
FIG. 12 is a perspective, schematic view of a distal end of the subcutaneous shunt.

A preferred embodiment of the distal end of shunt 18 is illustrated in FIG. 12 as including external and internal tubes 56 and 58, between which is located hemispherical spring 60. External tube 56 has a closed distal end 62 that is sealingly bonded between the external wall of tube 58 and tube 56. Projecting through end wall 62 of tube 58 is extension 64 including a one way, i.e., check, valve in the form of slit 66 which permits fluid inside of tube 58 to flow into peritoneum region 14. Because end wall 62 is sealed between external and interior tubes 56 and 58 a reservoir for CSF is formed between interior wall 56 and exterior of wall 58.

Cerebral spinal fluid flowing through openings 28 of catheter 16 accumulates in the reservoir between tubes 56 and 58 to control the pressure on the collapsible wall of internal tube 58. As the cerebral spinal fluid accumulates in the reservoir between tubes 56 and 58, cerebral spinal fluid also flows into internal tube 58, thence through check valve slit 66 in extension 64 of internal tube 58. The flow rate of cerebral spinal fluid through slit 66 into peritoneum 14 is determined by the amount of fluid in internal tube 58, the pressure exerted on the collapsible wall of tube 58 by the cerebral spinal fluid in the reservoir between the interior wall of tube 56 and the exterior wall of tube 58, and the pressure difference between the fluid in tube 56 and atmospheric pressure.

Figure 13:
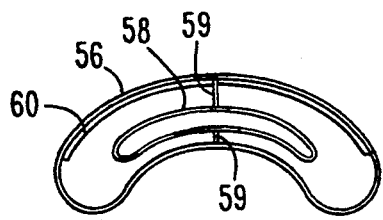
FIGS. 13 and 14 are cross sectional views of the structure illustrated in FIG. 11 when the intracranial pressures are respectively less than and greater than atmospheric.
Figure 14:
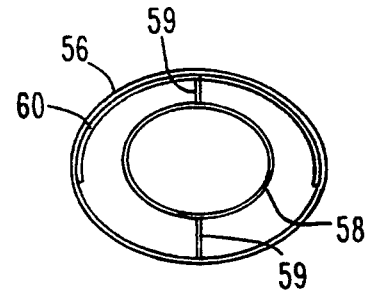

The cross sectional area and shape of tubes 56 and 58 vary as the pressure of the fluid between tubes 56 and 58 (the intracranial pressure) changes relative to atmospheric pressure as illustrated in FIGS. 13 and 14. When the CSF pressure between tubes 56 and 58 is less than atmospheric the cross sectional areas of tubes 56 and 58 decrease to restrict the flow of CSF through slit 66, as illustrated in FIG. 13. Tubes 56 and 58 change from the oval cross sections illustrated in FIG. 11 to kidney cross sections illustrated in FIG. 13 when the intracranial pressure is less than atmospheric. The walls of tubes 56 and 58 under this circumstance are such that the "top" wall portions thereof closest to skin 61 have a greater radius of curvature than the wall portions closest to inner fascia 63. The adjacent wall portions of tubes 54 and 56 move together and change size and shape because of (a) the pressure exerted by the atmosphere through tube 56 on the fluid in the reservoir between the tubes, (b) the pressure exerted by the fluid in the reservoir on the fluid in tube 58 and, (c) the mechanical connections of sturts 59 between the tubes. The "top" wall portion of tube 56 does not change shape as much as the "bottom" portion because spring 60 abuts against the top portion to inhibit substantial changes in the shape thereof.

For CSF pressures between tubes 56 and 58 greater than atmospheric, the cross sectional areas of 56 and 58 increase to increase the flow rate of CSF through slit 66, as illustrated in FIG. 14. Tubes 56 and 58 change from the relatively high ratios of the major to minor axis lengths illustrated in FIG. 11 to ellipses having close to unity major to minor axis ratios for intracranial pressures greater than atmospheric. The "bottom" wall portions of tubes 56 and 58 become more curved because of the greater pressure compliance of the bottom wall portions than the top wall portions which results from the failure of the bottom wall portion of tube 56 to be constrained by spring 60. This permits the higher than atmospheric intracranial pressure of the CSF between tubes 56 and 58 to force the bottom portion of tube 56 outwardly. The outward motion of tube 56 is followed by outward movement of the bottom portion of tube 58, to increase the cross sectional area of tube 58.

Figure 12A:
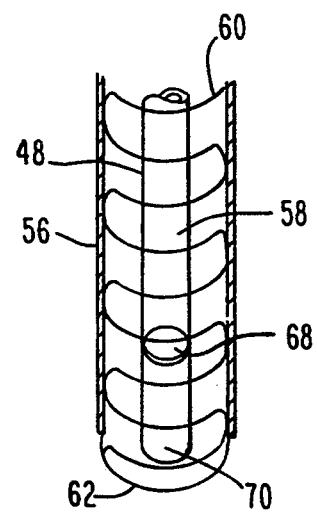
FIG. 12a is a perspective, schematic view of an alternate embodiment of the structure illustrated in FIG. 12.

An alternate structure at the distal end of shunt 18 is illustrated in FIG. 12a wherein extension 64 is eliminated and slit 66 is replaced by check valve 68 that is fixed in the interior of internal tube 58 close to wall 62. Check valve 68 is preferably a one-way low pressure conventional miter valve, located just above distal opening 70 in internal tube 58. Valve 68 is maintained in situ by spring 60 or by a pair of opposing flange-like ledges longitudinally spaced from each other along the wall of internal tube 58.

Figure 15:
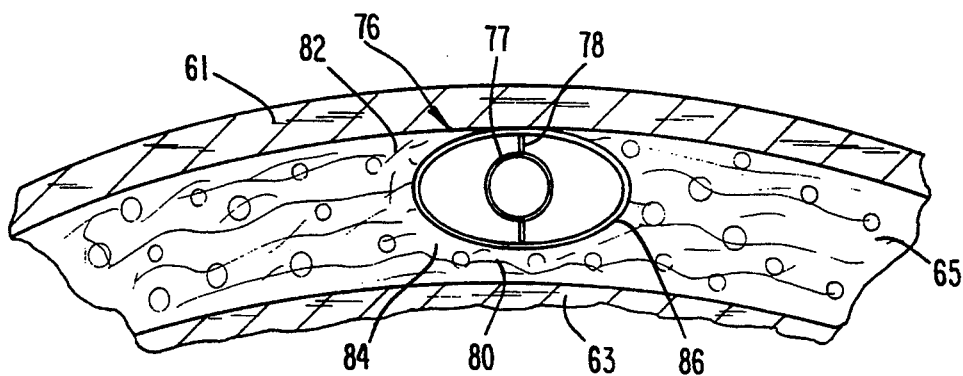
FIG. 15 is a cross sectional view of an alternate embodiment of the subcutaneous shunt when intracranial pressure is approximately atmospheric.

In accordance with a further embodiment of the invention, illustrated in FIG. 15, tube 56 and spring 60 are replaced by external elliptical cross-sectioned tube 76 having a relatively thick "top" wall portion and a more compliant thin "bottom" wall portion. Inner tube 58 is replaced by tube 77 having approximately a circular cross section when the intracranial pressure of the CSF between tubes 76 and 77 is approximately at atmospheric pressure. Membranes 78 and 80 extend along the minor axis of the ellipse between the exterior wall of internal tube 77 and the interior wall of external tube 76 to connect these tubes together. More than one-half of the exterior cross sectional surface of external tube 76, defined by portion 82 between points 84 and 86, has a thickness considerably greater than the remainder of the tube. Portion 82 extends from a point on one side of the major axis of the elliptical cross section of tube 76, past the major axis of the ellipse, past the minor axis of the ellipse, past the opposite side of the major axis, to a point below the major axis.

Figure 16:
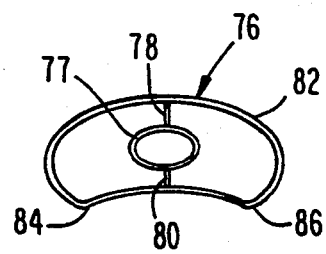
FIG. 16 is a cross sectional view of the structure illustrated in FIG. 15 for lower than atmospheric intracranial pressure.
Figure 17:
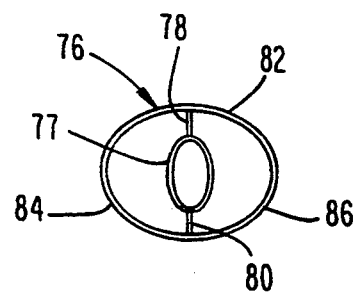
FIG. 17 is a view of the structure illustrated in FIG. 15 for higher than atmospheric intracranial pressure.

The construction of external tube 76, internal tube 77 and membranes 78 and 80 is such that the external tube has the stated elliptical cross shape and the internal tube has a circular cross-section, as illustrated in FIG. 15, when the intracranial pressure of the cerebral spinal fluid between tubes 76 and 77 is approximately at atmospheric pressure. When the intracranial pressure of the cerebral spinal fluid between tubes 76 and 77 is lower than atmospheric, there are reductions in cross sectional areas of tubes 76 and 77 and tube 76 assumes a kidney-type shape, causing the cross section of internal tube 77 to become elliptical, as illustrated in FIG. 16. The major axis of the elliptical cross section of internal tube 77 is generally in the same direction as the major axis of the ellipse of external tube 76. If, however, the intracranial pressure of the cerebral spinal fluid between tubes 76 and 77 is higher than atmospheric, the cross-section of external tube 76 becomes somewhat circular, as illustrated in FIG. 17. The resulting decrease and increase in lengths of the major and minor axes of tube 76 causes the cross-section area of internal tube 77 to increase. The shape of internal tube 77 changes to form an ellipse having a major axis that is generally in the same direction as the minor axis of external tube 76. The compliance of the material forming external tube 76 is much less than the compliance of internal tube 77, so there is a considerably larger change in cross sectional area of the internal tube for a unit change of pressure than for external tube 56. Thereby, the same overall effect on the flow of CSF to peritoneum 14 is provided by the structures illustrated in FIGS. 12 and 15.

While there have been described and illustrated specific embodiments of the invention, it will be clear that variations in the details of the embodiments specifically illustrated and described may be made without departing from the true spirit and scope of the invention as defined in the appended claims.

I claim:

1. A shunt for the flow of cerebrospinal fluid between brain ventricles and a peritoneum region of a subject comprising a first tube having openings positioned for supplying the fluid only from the brain ventricles to the peritoneum region, a second tube surrounding and extending most of the length of the first tube and arranged so the fluid from the brain ventricles is resident in the second tube and does not flow to the peritoneum region, the first tube being constructed so the fluid in the second tube exerts pressure through a wall of the first tube on the fluid in the first tube, the first and second tubes being constructed so that in response to the volume of fluid in the second tube increasing there is an increase in pressure transmitted from fluid in the second tube to the first tube wall and the resulting increase in pressure on the first tube wall is transmitted to the fluid in the first tube and vice versa for decreases in the fluid volume in the second tube.

2. The shunt of claim 1 wherein the first tube includes a one-way valve for flow of the cerebrospinal fluid from the first tube into the peritoneum region.

3. The shunt of claim 1 wherein the wall of the first tube is collapsible so the wall of the first tube moves toward the center of the first tube in response to the pressure on the exterior of the wall of the first tube exceeding the pressure on the interior of the wall of the first tube and vice versa.

4. The shunt of claim 3 wherein the wall of the second tube is collapsible so the wall of the second tube moves toward the wall of the first tube in response to the pressure on the exterior of the wall of the second tube exceeding the pressure on the interior of the wall of the second tube and vice versa.

5. The shunt of claim 4 wherein the compliance of the first tube is greater than that of the second tube.

6. The shunt of claim 1 wherein the wall of the second tube is collapsible so the wall of the second tube moves toward the wall of the first tube in response to the pressure on the exterior of the wall of the second tube exceeding the pressure on the interior of the wall of the second tube and vice versa.

7. The shunt of claim 1 wherein the first and second tubes are constructed and arranged so the first tube has a cross-sectional area (a) in a first range in response to pressure of the fluid on an interior wall of the second tube having a neutral value associated with the pressure on the interior wall approximating atmospheric pressure, (b) in a second range in response to pressure of the fluid on the interior wall of the second tube having a value in excess of atmospheric pressure and (c) in a third range in response to the pressure of the fluid on the interior wall of the second tube having a value less than atmospheric pressure, wherein the values in the second and third ranges are respectively greater and less than the values in the first range.

8. The shunt of claim 7 wherein the first and second tubes are constructed and arranged so the first tube has (a) a first oval-like cross-sectional area in response to pressure of the fluid on an interior wall of the second tube having the neutral value, (b) a second oval-like cross-sectional area with a longer major axis than the first oval-like cross in response to pressure of the fluid on the interior wall of the second tube having a value in excess of atmospheric pressure and (c) circular-like cross-section in response to the pressure of the fluid on the interior wall of the second tube having a value less than atmospheric pressure, wherein the values in the second and third ranges are respectively greater and less than the values in the first range.

9. The shunt of claim 7 wherein the first and second tubes are constructed and arranged so the first tube has (a) a first oval-like cross-sectional area in a first range in response to pressure of the fluid on an interior wall of the second tube having a neutral value associated with the pressure on the interior wall approximating atmospheric pressure, (b) an oval-like cross-sectional area with a major axis in a first direction in response to pressure of the fluid on the interior wall of the second tube having a value in excess of atmospheric pressure and (c) an oval-like cross-sectional area with a major axis in a second direction generally at right angles to the first direction in response to the pressure of the fluid on the interior wall of the second tube having a value less than atmospheric pressure, wherein the values in the second and third ranges are respectively greater and less than the values in the first range.

10. The shunt of claim 7 wherein the second tube includes a structure so (a) a first wall portion of the second tube adjacent skin of the subject has a greater radius of curvature than a second wall portion of the second tube adjacent inner fascia of the subject in response to the pressure of the fluid on the interior wall of the second tube having a value less than atmospheric pressure, the radii of curvature having centers on the same side of the second wall portion in response to the pressure of the fluid on the interior wall of the second tube having a value less than atmospheric pressure, and (b) the first and second wall portions having oppositely directed curvatures relative to the center of the first tube in response to the pressure of the fluid on the interior wall of the second tube having a value greater than atmospheric pressure.

11. The shunt of claim 10 wherein the structure in the second tube includes a spring.

12. The shunt of claim 11 wherein the spring bears against the interior wall of the second tube and is made of a plastic material that does not cut through the second tube.

13. The shunt of claim 11 wherein the spring has plural axially spaced hemispherical sections bearing against the first wall portion to inhibit collapse of the first wall portion and second wall portion is relatively free to collapse.

14. The shunt of claim 13 wherein ends of adjacent ones of the hemispherical sections are connected together.

15. The shunt of claim 10 wherein the first wall portion of the second tube is stiffer and has a greater extent around the perimeter of the second tube than the second wall portion of the second tube in response to the pressure of the fluid on the interior wall of the second tube having a value approximately equal to atmospheric pressure.

16. The shunt of claim 15 wherein a portion of the first tube facing the first wall portion of the second tube is mechanically connected to an interior segment of the first wall portion about half way between opposite ends of the first wall portion and a region of the first tube facing the second wall portion of the second tube is mechanically connected to an interior segment of the second wall portion about half way between opposite ends of the second wall portion.

17. The shunt of claim 1 further including a ventricular catheter for supplying fluid from the brain ventricles to the interiors of said first and second tubes.

18. The shunt of claim 17 wherein the catheter includes a wall having plural openings positioned and arranged (a) so cerebrospinal fluid flows from the brain ventricles through the catheter to the interiors of the first and second tubes, and (b) to prevent non-fluid material of the subject from occluding the flow of cerebrospinal fluid from the brain ventricles through the catheter to the interiors of the first and second tubes.

19. The shunt of claim 18 wherein all of the plural openings are axially spaced from each other along the length of the catheter.

20. The shunt of claim 19 wherein the plural openings are positioned at different angles about the catheter wall.

21. The shunt of claim 20 further including a member within the catheter in a region extending across first and second of said openings to divide the region into first and second chambers so non-fluid material from the subject entering the first chamber through the first opening is inhibited from (a) entering the second chamber and (b) traversing the second opening, and non-fluid material from the subject entering the second chamber through the second opening is inhibited from (a) entering the first chamber and (b) traversing the first opening.

22. The shunt of claim 21 wherein the first and second openings are on portions of the catheter wall that are spaced from each other by about 180°.

23. The shunt of claim 20 wherein the catheter wall includes first, second, third and fourth of the openings, the first and second openings being on portions of the catheter wall that are spaced from each other by about 180°, the third and fourth openings being on portions of the catheter wall that are spaced from each other by about 180° and from the first and second openings by about 90°, first and second members respectively positioned at first and second axially displaced regions within the catheter, the first member dividing the first region into first and second chambers and being approximately at right angles to the first member, the second member dividing the second region into third and fourth chambers, the first, second, third and fourth openings respectively opening into the first, second, third and fourth chambers, the members, openings and chambers being arranged so non-fluid material from the subject entering one of the chambers through the opening of that chamber is inhibited from (a) entering the other chambers and (b) traversing the other openings.

24. The shunt of claim 1 further including a ventricular catheter for supplying fluid from the brain ventricles to said first and second tubes, the catheter including a collapsible wall, and mechanical means within the catheter for inhibiting collapsing and/or kinking of the catheter wall.

25. The shunt of claim 24 wherein the mechanical means includes a spring bearing against interior portions of the catheter wall.

26. The shunt of claim 25 wherein the spring bears against a proximal end of the interior of the catheter wall.

27. The shunt of claim 25 wherein the spring bears against proximal and distal ends of the interior of the catheter wall.

28. The shunt of claim 25 wherein the spring includes first and second connected segments respectively bearing against proximal and distal ends of the interior of the catheter wall.

29. The shunt of claim 28 wherein the spring includes a strut axially extending in the catheter and connecting the first and second segments together.

30. The shunt of claim 24 wherein the wall includes plural openings positioned and arranged (a) so cerebrospinal fluid flows from the brain ventricles through the catheter to the interiors of the first and second tubes, and (b) to prevent non-fluid material of the subject from occluding the flow of cerebrospinal fluid from the brain ventricles through the catheter to the interiors of the first and second tubes.

31. A catheter for directing fluid from an interior portion of a subject where a proximal end of the catheter is located to a distal end thereof comprising a tube for draining the fluid from the subject, the tube having a wall with plural openings positioned and arranged (a) so the fluid flows from the proximal end through the catheter to the distal end and (b) to prevent non-fluid material of the subject from occluding the flow of the fluid from a site of the fluid through the catheter to the distal end, all of the plural openings being axially spaced from each other along the length of the tube wall, the plural openings being positioned at different angles about the tube wall, a member within the catheter in a region extending across first and second of said openings to divide the region into first and second chambers so non-fluid material from the subject entering the first chamber through the first opening is inhibited from (a) entering the second chamber and (b) traversing the second opening and non-fluid material from the subject entering the second chamber through the second opening is inhibited from (a) entering the first chamber and (b) traversing the first opening.

32. The catheter of claim 31 wherein the first and second openings are on portions of the catheter wall that are spaced from each other by about 180°.

33. A catheter for directing fluid from an interior portion of a subject where a proximal end of the catheter is located to a distal end thereof comprising a tube for draining the fluid from the subject, the tube having a wall with plural openings positioned and arranged (a) so the fluid flows from the proximal end through the catheter to the distal end and (b) to prevent non-fluid material of the subject from occluding the flow of the fluid from a site of the fluid through the catheter to the distal end, all of the plural openings being axially spaced from each other along the length of the tube wall, the plural openings being positioned at different angles about the tube wall, the catheter wall including first, second, third and fourth of the openings, the first and second openings being on portions of the catheter wall that are spaced from each other by about 180°, the third and fourth openings being on portions of the catheter wall that are spaced from each other by about 180° and from the first and second openings by about 90°, first and second members respectively positioned at first and second axially displaced regions within the catheter, respectively, the first member dividing the first region into first and second chambers and being approximately at right angles to the first member, the second member dividing the second region into third and fourth chambers, the first, second, third and fourth openings respectively opening into the first, second, third and fourth chambers; the members, openings and chambers being arranged so non-fluid material from the subject entering one of the chambers through the opening of that chamber is inhibited from (a) entering the other chambers and (b) traversing the other openings.

34. A catheter for directing fluid from an interior portion of a subject where a proximal end of the catheter is located to a distal end thereof comprising a tube for draining the fluid from the subject, the tube having a wall with plural openings positioned and arranged (a) so the fluid flows from the proximal end through the catheter to the distal end and (b) to prevent non-fluid material of the subject from occluding the flow of the fluid from a site of the fluid through the catheter to the distal end, a member within the catheter in a region extending across first and second of said openings to divide the region into first and second chambers so non-fluid material from the subject entering the first chamber through the first opening is inhibited from (a) entering the second chamber and (b) traversing the second opening and non-fluid material from the subject entering the second chamber through the second opening is inhibited from (a) entering the first chamber and (b) traversing the first opening.

35. The catheter of claim 34 wherein the first and second openings are on portions of the catheter wall that are spaced from each other by about 180°.

36. The catheter of claim 34 wherein the catheter wall includes first, second, third and fourth of the openings, the first and second openings being on portions of the catheter wall that are spaced from each other by about 180°, the third and fourth openings being on portions of the catheter wall that are spaced from each other by about 180° and from the first and second openings by about 90°, first and second members respectively positioned at first and second axially displaced regions within the catheter, respectively, the first member dividing the first region into first and second chambers and being approximately at right angles to the first member, the second member dividing the second region into third and fourth chambers, the first, second, third and fourth openings respectively opening into the first, second, third and fourth chambers; the members, openings and chambers being arranged so non-fluid material from the subject entering one of the chambers through the opening of that chamber is inhibited from (a) entering the other chambers and (b) traversing the other openings.

* * * * *